United States Patent [19]

Stadtmueller

[11] Patent Number: 5,000,954
[45] Date of Patent: Mar. 19, 1991

[54] THRUSH TREATMENT COMPOSITION AND METHOD

[76] Inventor: Ludwig A. Stadtmueller, 1232 Cambridge Ave., Plainfield, N.J. 07062

[21] Appl. No.: 427,577

[22] Filed: Oct. 27, 1989

[51] Int. Cl.$^5$ .................. A61K 35/78; A61K 33/48; A61K 33/26; A61K 33/06

[52] U.S. Cl. .................. 424/196.1; 424/61; 514/638; 514/648; 514/697

[58] Field of Search .............. 424/61, 196.1; 514/638, 514/648, 697

[56] References Cited

U.S. PATENT DOCUMENTS

| | | | |
|---|---|---|---|
| 4,070,451 | 1/1978 | Price | 424/61 |
| 4,822,595 | 4/1989 | Corliss et al. | 424/61 |
| 4,859,694 | 8/1989 | Pavlich | 424/61 |

OTHER PUBLICATIONS

*The Merck Index*, Ninth Edition (1976), Merck & Co., Inc., Rahway, NJ, p. 566, Entry 4227.

*Primary Examiner*—Frederick E. Waddell
*Attorney, Agent, or Firm*—Kenneth P. Glynn

[57] ABSTRACT

The present invention is directed to a composition of matter for and method of treating thrush and other equine infections. The composition includes the following: a. about 20% to about 35% by weight of formaldehyde and/or an active derivative thereof; b. about 5% to about 20% by weight of turpentine; c. about 10% to about 25% by weight of gentian violet; d. balance being an oily diluent. The preferred diluent is mineral oil. The method involves applying an effective amount of the composition to the diseased area.

12 Claims, No Drawings

THRUSH TREATMENT COMPOSITION AND METHOD

BACKGROUND OF THE INVENTION

1. Field of the Invention

The present invention is directed to a composition for the treatment of thrush, such as equine thrush, and a method of treating thrush. The composition includes three critical elements including formaldehyde or its derivative, turpentine and gentian violet, along with a diluent. The method of the present invention involves using an effective amount of the composition, either topically or otherwise, on the affected area.

2. Prior Art Statement

Thrush is a well known and long recognized suppurative disease which spreads over time on affected areas of an animal such as a horse or donkey, destroying the frog and leaving open sores which eventually create significant pain and tenderness to the animal. Many treatments have been developed over the years and some utilize formalin or formaldehyde while others use metalo-organic compounds such as copper niacyanate. While these compositions treat some of the symptoms of thrush effectively, they do not always eliminate the thrush and frequently require multiple treatments before being effective.

The present invention composition and method have been found to frequently totally eliminate thrush with a single application.

SUMMARY OF THE PRESENT INVENTION

The present invention is directed to a composition of matter for and method of treating thrush. The composition includes the following: a. about 20% to about 35% by weight of formaldehyde and/or an active derivative thereof; b. about 5% to about 20% by weight of turpentine; c. about 10% to about 25% by weight of gentian violet; and, d. balance being an oily diluent. The preferred diluent is mineral oil. The method involves applying an effective amount of the composition to the diseased area.

DETAILED DESCRIPTION OF THE INVENTION

The present invention, as indicated, is directed a composition of matter and a method for treating thrush. Thrush is a disease common to many animals including those in the equine family and is a type of suppurative disorder. Many types of materials have been used over the years for the treatment of thrush and most, if not all, tend to merely temporarily alleviate the symptoms rather than treat and cure the disease itself. However, it has been discovered that the present invention totally eliminates the disease and very often accomplishes this with a single application.

The present invention composition, as mentioned, contains about 20%-35 % by weight of formaldehyde and/or an active derivative of formaldehyde as well as about 5%-20% by weight of turpentine, about 10%-25 % by weight of gentian violet and the balance being a diluent such as an oily diluent. The principle active ingredient are the formaldehyde or derivative, the turpentine and the gentian violet. Further, it is recognized that the action of the formaldehyde may still be achieved by using an active derivative thereof such as a compound formaldehyde or an acid of a formaldehyde or its derivative.

While 20%-35% by weight of the formaldehyde component is utilized in the present invention, at least about 25%-35% is preferably used. Likewise, with regard to the turpentine, generally 5%-20% may be used but preferably about 5% to about 15% by weight is used. Finally, as to the gentian violet, in general 10%-25% by weight may be used and preferably 15% to about 25% is used.

The gentian violet used herein is one of a family of products which has been known for many years and is the hydrochloride, sulfate or nitrate of triphenylrosaniline and triphenylpararosaniline.

The present invention treatment is applied externally but may also be applied by injection into the areas which are diseased. In general, the present invention composition, including its diluent, may be used in any known applicator such as a squeeze bottle or the like and this is applied topically to the "foot frog" and particularly around the edges and the center of the frog. Supplementally, cotton batting or the like may be used to keep the composition from being absorbed by the soil or other ground on which the horse may be resting. By applying the composition of the present invention in the manner stated, it is important that penetration into the cleft be achieved so as to enhance the likelihood of complete irradication of the disease in a single shot. In the event present invention composition is injected, this also acts to rapidly cure the ailment.

In addition to thrush treatment, the present invention composition may be used to stop summer sores and can be injected into the problem areas. Summer sores are typically caused by cutaneous habronemiasis, or caused by the stomach worm. By injection into the sores, the present invention composition acts to kill off any of the microorganisms or organisms causing the problem.

The diluent is mentioned to be mineral oil although any equivalent inert carrier may be used such as petroleum jelly, vegetable oil, soybean oil or the like. Additionally, the functional equivalent of the formaldehyde, as mentioned, may be used as a total substitute for the formaldehyde or in combination with the formaldehyde.

It should now be seen that the present invention embodies a number of variations and the artisan should be able to vary the formulations without exceeding scope of the present invention.

EXAMPLE 1

A three year old thorobred mare was found to have all four feet heavily infected with thrush. On the bottoms, the protective frog was rotted away and maggots were habitating both front hoof frogs. Having found and tested prior art treatments in the past to be uneffective or requiring many applications, formulation of the present invention was prepared for treatment, as follows:

The following were mixed into solution:

| (1) | formaldehyde | 1.5 oz. (27.3%) |
| (2) | gentian violet | 1 oz. (18.2%) |
| (3) | turpentine | 0.5 oz. (9.1%) |
| (4) | mineral oil as diluent | 2.5 oz. (45.5%) |
| | TOTAL | 5.5 oz. (100%) |

The solution was applied by squeeze bottle by squirting into the deep cleft of the frog until it is dripping saturated and then the deep cleft is packed with cotton batting. The packing was then squirted until saturated.

Three days later all four hooves were found to be clean. All evidence of thrush was gone and new frog tissue was growing.

EXAMPLE 2

Arabian horses and quarterhorses are found to have summer sores (Hebronemiasis). These are caused by wounds or abrasions and the eggs hatch into larvae that dwell in the raw areas for nutrients causing infection. As these feed upon the wounds, pus is exuded and the infection is very difficult to cure. The spread of infection becomes semi-dormant or dormant during the winter months but reactivates in the warmer weather.

Formulations identical to and similar to the Example 1 formula above are injected into the opening where the larvae enter the wound. The injections are made by syringe and only about 1 c.c. of solution is used for each opening.

The worms (larvae) are destroyed and the sores heal from the inside out. It has been found that healing is completed in about two weeks.

What is claimed is:

1. A composition of matter which comprises a mixture of the following:
   (a.) about 20% to about 35% by weight of formaldehyde and/or an active derivative thereof;
   (b.) about 5% to about 20% by weight of turpentine;
   (c.) about 10% to about 25% by weight of gentian violet; and,
   (d.) balance being an oily diluent.

2. The composition of claim 1 wherein said oily diluent is mineral oil or an equivalent inert diluent.

3. The composition of claim 1 wherein said oily diluent is selected from mineral oil, vegetable oil, and petroleum derivatives; such as petroleum jelly.

4. The composition of claim 1 wherein said oily diluent is a mixture of oils.

5. A composition of matter which comprises a mixture of the following:
   (a.) about 25% to 35% by weight of formaldehyde and/or an active derivative thereof;
   (b.) about 5% to about 15% by weight of turpentine;
   (c.) about 15% to about 25% by weight of gentian violet; and,
   (d.) balance being an oily diluent.

6. The composition of claim 5 wherein said oily diluent is mineral oil or an equivalent inert diluent.

7. The composition of claim 5 wherein said oily diluent is selected from mineral oil, vegetable oil, and petroleum derivatives, such as petroleum jelly.

8. The composition of claim 5 wherein said oily diluent is a mixture of oils.

9. A method of treating thrush equine infections, comprising applying onto the infected area an effective amount of a composition containing:
   (a.) about 20% to about 35% by weight of formaldehyde and/or an active derivative thereof;
   (b.) about 5% to about 20% by weight of turpentine;
   (c.) about 10% to about 25% by weight of gential violet; and,
   (d.) balance being an oily diluent.

10. The method of claim 9 wherein said oily diluent is mineral oil or an equivalent inert diluent.

11. The method of claim 9 wherein said oily diluent is selected from mineral oil, vegetable oil, and petroleum derivatives; such as petroleum jelly.

12. The method of claim 9 wherein said oily diluent is a mixture of oils.

* * * * *